United States Patent
Stehle et al.

(10) Patent No.: US 6,819,423 B2
(45) Date of Patent: Nov. 16, 2004

(54) HIGH SPATIAL RESOLUTION INFRARED ELLIPSOMETER

(75) Inventors: Jean-Louise Stehle, Colombes (FR); Pierre Boher, Yerres (FR); Michel Luttmann, Le Barp (FR)

(73) Assignee: Societe de Production et de Recherches Appliquees, Bois-Colmbes (FR)

( * ) Notice: Subject to any disclaimer, the term of this patent is extended or adjusted under 35 U.S.C. 154(b) by 163 days.

(21) Appl. No.: 10/333,416

(22) PCT Filed: Jun. 28, 2001

(86) PCT No.: PCT/FR01/02072
§ 371 (c)(1),
(2), (4) Date: Jan. 16, 2003

(87) PCT Pub. No.: WO02/06780
PCT Pub. Date: Jan. 24, 2002

(65) Prior Publication Data
US 2004/0027571 A1 Feb. 12, 2004

(30) Foreign Application Priority Data
Jul. 17, 2000 (FR) ............................................ 00 09318

(51) Int. Cl.$^7$ .................................................. G01J 4/00
(52) U.S. Cl. ...................................................... 356/369
(58) Field of Search .............................. 356/369, 237.1, 356/237.2, 237.3, 237.4, 237.5, 364, 365, 366, 367, 368

(56) References Cited

U.S. PATENT DOCUMENTS 3,799,679 A    3/1974  Simko
3,857,637 A  * 12/1974  Obenreder ................... 356/613
5,329,357 A  *  7/1994  Bernoux et al. ............. 356/369
5,485,271 A    1/1996  Drevillon et al.

(List continued on next page.)

FOREIGN PATENT DOCUMENTS

| EP | 0 558 863 A1 | 9/1993 |
| EP | 0 843 811 B1 | 7/2002 |
| JP | 9-318315 A | 12/1997 |
| JP | 9-318315 | 12/1997 |

OTHER PUBLICATIONS

International Search Report of PCT/FR01/02072, dated Oct. 25, 2001.

(List continued on next page.)

*Primary Examiner*—Michael P. Stafira
*Assistant Examiner*—Juan D Valentin, II
(74) *Attorney, Agent, or Firm*—Christie, Parker & Hale, LLP

(57) ABSTRACT

The invention concerns an ellipsometer comprising a source (S) supplying at least an infrared radiation, a sample-holder (PE), a sensor (D), a first optical system mounted between the source (S) and the sample-holder (PE), so as to illuminate a sample placed on the sample-holder, under oblique view with a polarised light beam and a second optical system mounted between the sample-holder (PE) and the sensor (D) for collecting the light reflected by the sample. The ellipsometer further comprises a blocking device (F2) mounted on the reflection path in the focal plane of the focusing device (M2) of the second optical system, and adapted to block parasite rays (RP) derived from the rear surface (FAR) of the sample and to allow through useful rays (RU) derived from the front surface (FAV) of the sample towards the sensor (D), thereby enabling to obtain a resolution with respect to the sample front and rear surfaces.

20 Claims, 2 Drawing Sheets

U.S. PATENT DOCUMENTS

Figure 1:
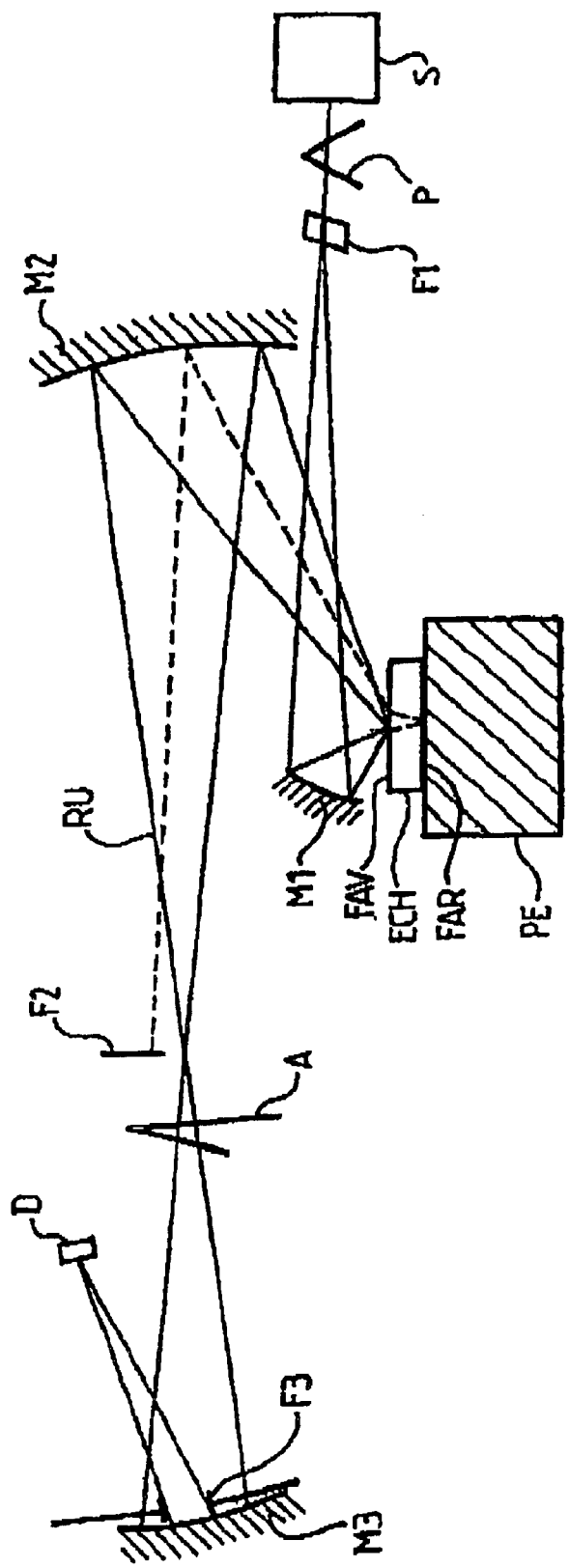

| | | | |
|---|---|---|---|
| 5,706,212 A | | 1/1998 | Thompson et al. |
| 5,859,424 A | * | 1/1999 | Norton et al. ............... 250/226 |
| 5,910,842 A | | 6/1999 | Piwonka-Corle et al. |
| 5,991,037 A | | 11/1999 | Piel et al. |
| 6,088,092 A | | 7/2000 | Chen et al. |
| 6,088,104 A | | 7/2000 | Peterson |
| 6,097,482 A | | 8/2000 | Smith et al. |
| 6,130,749 A | | 10/2000 | Meeks et al. |
| 6,134,012 A | * | 10/2000 | Aspnes et al. ............... 356/369 |
| 6,166,808 A | | 12/2000 | Greve |
| 6,184,984 B1 | | 2/2001 | Lee et al. |
| 6,392,749 B1 | | 5/2002 | Meeks et al. |
| 6,456,376 B1 | * | 9/2002 | Liphardt et al. ............ 356/369 |
| 6,710,881 B1 | * | 3/2004 | Ngoi et al. .................. 356/487 |
| 2002/0113200 A1 | | 8/2002 | Hajjar et al. |

OTHER PUBLICATIONS

International Preliminary Examination Report of PCT/FR01/02072, dated Mar. 11, 2002.

DATABASE WPI, Section EI, Week 199809, Derwent Publications Ltd., London, GB; Class S02, AN 1998–090673 XP002163558.

Azzam, R.M.A. et al., *ellipsometry and polarized light*, Elsevier Science Publishers B.V., 1977, 1987, §5.4.4, pp 397–398.

Röseler, A., *Infrared Spectroscopic Ellipsometry*, Akademie–Verlag Berlin, 1990, Chap. 3.1, p. 119, Chap. 3.5 pp 135–136.

Joerger, R. et al., *Influence of incoherent superposition of light on ellipsometric coefficients*, Applied Optics, vol. 36, No. 1, Jan. 1, 1997, pp 319–327.

Horie, M., *Simple birefringence measurement method for coated optical disks with a fixed incident angle ellipsometer*, Applied Optics, vol. 34, No. 25, Sep. 1, 1995, pp 5715–5719.

* cited by examiner

HIGH SPATIAL RESOLUTION INFRARED ELLIPSOMETER

CROSS-REFERENCE TO RELATED APPLICATION

This application is a National Phase Patent Application of International Application Number PCT/FR01/02072, filed on Jun. 28, 2001, which in turn claims priority to French Patent Application Number 00/09318, filed on Jul. 17, 2000.

The invention relates to the field of ellipsometry, and more particularly to ellipsometry operating in the infrared.

It has a general application in any field in which ellipsometry is used, and more particularly in microelectronics, in the optical characterisation of a sample, in the optical control of a surface treatment, or in the study of the growth of thin layers, for example of semiconductor materials, and of their interfaces. It also has an application in the cleaning, polishing and preparation of surfaces, in particular.

Ellipsometric measurements can be carried out at a fixed wavelength (monochromatic ellipsometry) or at several wavelengths (spectroscopic ellipsometry).

Depending upon the wavelength range of the source: ultraviolet, visible, near infrared, infrared, etc., it is possible to attain different properties of the layers, of the materials or to explore different materials.

In practice, the infrared is generally better adapted than the visible to attain the voluminal properties of the layers and of the materials.

In general, an ellipsometer operating in the infrared comprises:
  a source of light radiation supplying at least one infrared beam;
  a sample holder intended to carry a sample of a given thickness and comprising a front face and a rear face;
  a detector;
  a first optical system mounted between the source and the sample holder, and comprising a polariser and a focusing device in order to illuminate the sample placed on the sample holder under oblique incidence by a beam of polarised light; and
  a second optical system mounted between the sample holder and the detector and comprising a focusing device and an analyser to collect the light reflected by the sample.

Because of the very strict requirements in the manufacture of semiconductors there is a need for an ellipsometer having a high spatial resolution and the best possible accuracy of measurement.

With a transparent or semi-transparent sample of a given thickness, such as silicon, the rear face of the sample can disrupt the ellipsometric measurements by reflecting the stray radiation which contaminates the detection and the processing of the useful signal.

This contamination is difficult to deal with because the reflection coefficient of the rear face of a silicon substrate is not always known. The absorption coefficient k of the substrate is also not always known. Interference phenomena can also occur with this rear face. Likewise, phenomena of diffusion and/or of diffraction n infrared can also occur on this rear face. Moreover the rear face may not be parallel to the front face, which can give rise to additional and unnecessary calculations because only the measurement of the front face is pertinent for the user.

Known solutions exist for elimination of the harmful effects brought about by the rear face of the sample, particularly the use of mechanical means such as means for dulling the rear face which renders the specular reflections emitted by the rear face negligible.

When the sample has a relatively great thickness, it is possible to separate the radiation emitted by the front face from the radiation emitted by the rear face. However, such a solution can only be achieved for samples of a great thickness, which limits its application.

Another known solution consists of taking absorbent samples (that is to say non-transparent samples, such as highly doped silicon), but this also limits the application of such a solution.

The object of the present invention is to remedy these drawbacks and to propose a high spatial resolution ellipsometer which operates in the infrared in which stray reflections due to the rear face of the sample are eliminated.

The present invention relates to an ellipsometer device of the type comprising:
  a source of light radiation supplying at least one infrared beam;
  a sample holder intended to carry a sample of a given thickness and comprising a front face and a rear face;
  a detector;
  a first optical system mounted between the source and the sample holder, and comprising a polariser and a focusing device in order to illuminate the sample placed on the sample holder under oblique incidence by a beam of polarised light; and
  a second optical system mounted between the sample holder and the detector and comprising a focusing device and an analyser to collect the light reflected by the sample.

According to a general definition of the invention, the ellipsometer device further comprises a blocking device mounted on the reflection path in the focal plane of the focusing device of the second optical system and capable of blocking the stray radiation emitted by the rear face of the sample and allowing the useful radiation emitted by the front face of the sample to pass through towards the detector, which makes it possible to obtain a separating power with regard to the front and rear faces of the sample.

For example, the blocking device is of the type constituted by a slot with adjustable dimensions, cutter with adjustable edge, or the like.

According to a first preferred embodiment of the invention, the ellipsometer device according to the invention further comprises a widening device mounted on the illumination path and capable of widening the illuminating beam on the focusing device of the first system and of widening the reflecting beam on the focusing device of the second optical system.

For example, the widening device is of the type constituted by a slot with adjustable dimensions, cutter with adjustable edge, divergent lens, or the like.

The numerical aperture of the focusing device of the first optical system is preferably chosen so as to obtain an illuminating beam of small size on the sample. For example the size of the illuminating beam on the sample is less than 40 microns×40 microns in the case of a light source of the laser type.

For example, the focusing devices of the first optical system as well as of the second optical system comprise at least one optical element belonging to the group formed by concave mirrors (for example elliptical, parabolic, spherical, etc.).

The numerical aperture of the focusing device of the second optical system is chosen to separate the beams reflected by the front and rear faces of the sample.

According to a second preferred embodiment of the invention the ellipsometer device according to the invention further comprises a selector device for angles of incidence, mounted on the reflection path downstream of the blocking device according to the direction of propagation of the light and capable of selecting, for the measurements by the detector, only the radiation reflected by the sample under oblique incidence within a predetermined range of angles of incidence.

The selector device is preferably of the type constituted by a slot with adjustable dimensions, cutter with adjustable edge, or the like.

In practice, the light source is of the laser type, operating at terahertz frequencies, or silicon carbide source, filament, plasma, or the like.

The polariser of the first optical system is preferably of the type having a grid, with or without a rotating compensator, assembly with several polarisers with grids, or the like.

Likewise, the analyser of the second optical system is of the type having a grid, with or without a rotating compensator, assembly with two polarisers with grids, or the like.

For example, the detector is of the type constituted by a mercury-cadmium and/or tellurium cell, liquid nitrogen or the like.

In practice, the sample holder is of the type constituted by a table which is movable in XYZ and/or in rotation, a suspended sample holder or the like.

Figure 2:
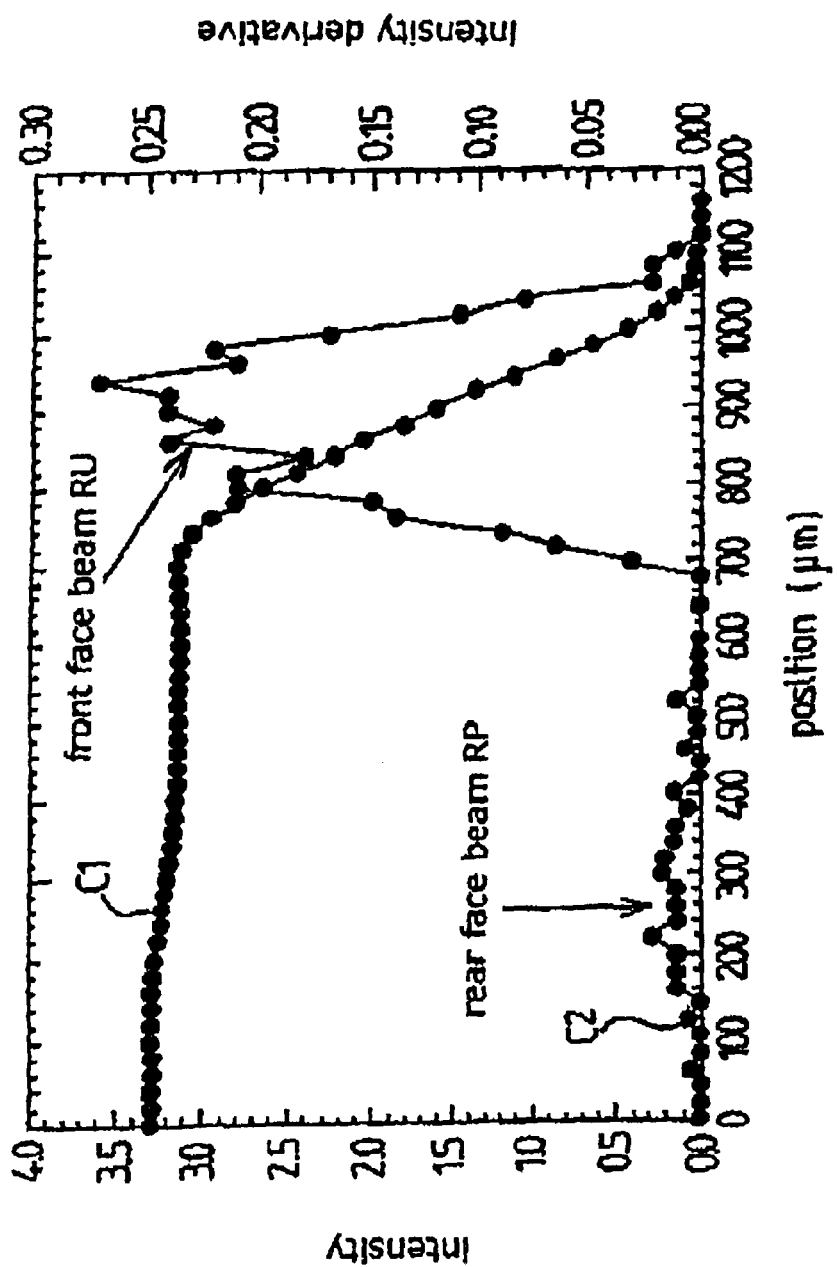

Other characteristics and advantages of the invention will become apparent in the light of the following detailed description and the drawings, in which:

FIG. 1 is a general diagram of an ellipsometer operating in the infrared according to the invention; and FIG. 2 shows the separating power of the blocking device according to the invention as a function of its position with respect to the light beams.

With reference to FIG. 1, a light source S supplies radiation in the infrared spectrum.

For example, the source S is of the silicon carbide type at 1200° K. Its spectral range is from 1.44 to 18 microns.

As a variant, the light source is of the type constituted by a laser operating at terahertz frequencies, a source with a filament, plasma or the like.

In spectroscopic ellipsometry, the illumination system includes an interferometer of the Michelson type mounted after the source and before the polariser in order to scan the spectral range of the apparatus.

A sample holder PE is intended to carry a sample ECH of a given thickness and comprising a front face FAV and a rear face FAR.

The sample is for example a silicon substrate with a thickness of the order of 400 to 700 microns.

The sample holder can be a table which is movable in XYZ and/or movable in rotation.

The sample holder can equally be a suspended sample holder.

Between the source S and the sample holder PE there is provided a first optical system comprising a polariser P and a focusing device M1. This first optical system makes it possible to illuminate the sample ECH placed on the sample holder PE, under oblique incidence by a beam of polarised light.

A widening device F1 is advantageously mounted on the illumination path. It can be placed upstream or downstream of the polariser according to the direction of propagation of the light. This widening device widens the illuminating beam on the mirror M1.

In practice, the widening device F1 is of the type constituted by a slot with adjustable dimensions, cutter with adjustable edge, divergent lens, or the like.

In practice, the numerical aperture of the mirror M1 is chosen so as to obtain an illuminating beam of small size on the sample.

For example, the size of the illuminating beam on the sample is less than 40 microns×40 microns within the framework of a laser source.

In practice, the mirror M1 which constitutes the focusing device of the first optical system is an elliptical mirror.

As a variant, this element M1 can be a parabolic mirror, a spherical mirror, a lens or even a dioptric, catadioptric optical unit or the like.

The polariser P is of the type constituted by a polariser with a grid with or without a rotating compensator. As a variant this polariser can comprise an assembly with two polarisers with grids or the like.

A second optical system is mounted between the sample holder PE and a detector D. This second optical system comprises a focusing device M2 and an analyser A to collect the light reflected by the sample.

The numerical aperture of the focusing device M2 of the second optical system is chosen so as to separate the beams reflected by the front face FAV and the rear face FAR of the sample.

The focusing device of the second optical system M2 comprises an optical element belonging to the group formed by concave mirrors (elliptical, parabolic or spherical), lenses and dioptric or catadioptric optical units or the like.

For example, the effective numerical aperture of the focusing device M2 of the second optical system is of the order of 2.5°.

The analyser A of the optical system is of the type constituted by a polariser with a grid with or without rotating compensator, assembly with two polarisers with grids, or the like. This analyser A is disposed on the reflecting path downstream of the second mirror M2.

The detector D is of the type constituted by a mercury-cadmium-tellurium cell, liquid nitrogen or the like. The detector is compatible with operation in the infrared.

Between the mirror M2 and the detector D there is advantageously provided another mirror M3 capable of focusing the reflecting beam onto the detector. The mirror M3 can be of the same type as the mirror M2.

A selector device for angles of incidence F3 is advantageously coupled to the mirror M3. This selector device F3 makes it possible to select, for the measurements by the detector D, only the radiation reflected by the sample under oblique incidence within a predetermined range of angles of incidence.

For example, the selector device F3 is of the type constituted by a slot with adjustable dimensions, cutter with adjustable edge, or the like.

According to the invention a blocking device F2 is provided which is mounted on the reflecting path in the focal plane of the focusing device M2 of the second optical system. This blocking device F2 is capable of blocking the stray radiation RP emitted by the rear face FAR of the sample and allowing the useful radiation RU emitted by the front face FAV of the sample to pass through towards the detector D.

Such a blocking device F2 makes it possible to obtain a separating power with regard to the front and rear faces FAV and FAR of the sample.

The blocking device F2 is advantageously of the type constituted by a slot with adjustable dimensions, cutter with adjustable edge, or the like.

The selector device F3 is advantageously positioned in front of the mirror M3 because if it were placed in front of the mirror M2 the diffractions due to the selector device F3 would be such that they would degrade the separating power of the blocking device according to the invention.

In a preferred embodiment of the invention an optical fibre is disposed between the source S and the first optical system P. Likewise another optical fibre is disposed between the second optical system M3 and the detector D.

FIG. 2 shows intensity curves C1 and intensity derivative curves C2 of the beam as a function of the position of the cutter F2 with respect to the normal of the beam.

The curves C1 and C2 demonstrate the effective separation of the beams from the front face and the rear face of the sample.

The present applicants have observed that when an ellipsometer according to the diagram as described in FIG. 1 is used, the ellipsometer has a separating power with regard to the front and rear faces of the sample which has a quite satisfactory value in order to carry out ellipsometric measurements in infrared on semiconductor materials such as silicon.

For example, the separating power is of the order of 400 microns with a light source with a wavelength of the order of 12 microns, a silicon substrate with a thickness of the order of 500 microns, a mirror M1 with an effective numerical aperture of 2.5°, a mirror M2 with an effective numerical aperture of the order of 2.5°, and an image of the slot F1 of the order of 300 microns.

In practice, the carrying out of the invention depends here upon the size of the spot, the quality of the optics, the thickness of the silicon substrate and the angle of incidence. For example, with an angle of incidence of 70° the separating power of the blocking device is of the order of 600 microns, with a mirror M2 having a magnification factor of 4.21.

What is claimed is:

1. Ellipsometer device of the type comprising:
   a source (S) of light radiation supplying at least one infrared beam;
   a sample holder (PE) intended to carry a transparent or semi-transparent sample (ECH) of a given thickness and comprising a front face and a rear face (FAV and FAR),
   a detector (D),
   a first optical system mounted between the source (S) and the sample holder (PE), and comprising a polariser (P) and a focusing device (M1) in order to illuminate the sample placed on the sample holder under oblique incidence by a beam of polarised light,
   a second optical system mounted between the sample holder (PE) and the detector (D) and comprising a focusing device (M2) and an analyser (A) to collect the light reflected by the sample,
   characterised in that it further comprises a blocking device (F2) mounted on the reflection path in the focal plane of the focusing device (M2) of the second optical system and capable of blocking the stray radiation (RP) emitted by the rear face (FAR) of the sample and allowing the useful radiation (RU) emitted by the front face (FAV) of the sample to pass through towards the detector (D), which makes it possible to obtain a separating power with regard to the front and rear faces of the sample.

2. Device as claimed in claim 1, characterised in that it comprises a selector device (M3, F3) for angles of incidence, mounted on the reflection path downstream of the blocking device according to the direction of propagation of the light and capable of selecting, for the measurements by the detector, only the radiation reflected by the sample under oblique incidence within a predetermined range of angles of incidence.

3. Device as claimed in claim 2, characterised in that the selector device (M3, F3) is of the type constituted by a slot with adjustable dimensions, cutter with adjustable edge, or the like.

4. Device as claimed in claim 1, characterised in that the blocking device (F2) is of the type constituted by a slot with adjustable dimensions, cutter with adjustable edge, or the like.

5. Device as claimed in claim 1, characterised in that it further comprises a widening device (F1) mounted on the illumination path and capable of widening the illuminating beam on the focusing device (M1) of the first system and of widening the reflecting beam on the focusing device (M2) of the second optical system.

6. Device as claimed in claim 5, characterised in that the widening device (F1) is of the type constituted by a slot with adjustable dimensions, cutter with adjustable edge, divergent lens, or the like.

7. Device as claimed in claim 1, characterised in that the numerical aperture of the focusing device (M1) of the first optical system is chosen so as to obtain an illuminating beam of small size on the sample.

8. Device as claimed in claim 7, characterised in that the size of the illuminating beam on the sample is less than 40 microns×40 microns.

9. Device as claimed in claim 1, characterised in that the focusing device (M1) of the first optical system comprises at least one optical element belonging to the group formed by concave mirrors, spherical mirrors, lenses, dioptric or catadioptric optical units or the like.

10. Device as claimed in claim 1, characterised in that the numerical aperture of the focusing device (M2) of the second optical system is chosen to separate the beams reflected by the front and rear faces of the sample.

11. Device as claimed in claim 1, characterised in that the focusing device (M2) of the second optical system comprises at least one optical element belonging to the group formed by concave mirrors, lenses, dioptric or catadioptric optical units and the like.

12. Device as claimed in claim 8, characterised in that the effective numerical aperture of the focusing device (M2) of the second optical system is of the order of 2.5°.

13. Device as claimed in claim 1, characterised in that the light source (S) is of the type constituted by a laser, terahertz, globar, filament, plasma, or the like.

14. Device as claimed in claim 1, characterised in that the polariser (P) of the first optical system is of the type constituted by a polariser having a grid, with or without a rotating compensator, assembly with two polarisers with grids, or the like.

15. Device as claimed in claim 1, characterised in that the analyser (A) of the second optical system is of the type constituted by a polariser having a grid, with or without a rotating compensator, assembly with two polarisers with grids, or the like.

16. Device as claimed in claim 1, characterised in that the detector (D) is of the MCT type or the like.

17. Device as claimed in claim 1, characterised in that the sample holder (PE) is of the type constituted by a table which is movable in XYZ and/or in rotation, a suspended sample holder or the like.

18. Device as claimed in claim 1, characterised in that it comprises an optical fibre between the source (S) and the first optical system.

19. Device as claimed in claim 1, characterised in that it comprises an optical fibre between the second optical system and the detector (D).

20. Device as claimed in claim 1, characterised in that the sample (ECH) is of the type constituted by a substrate made from semiconductor material such as silicon.

* * * * *